US00PP22545P3

(12) United States Plant Patent
Harris

(10) Patent No.: US PP22,545 P3
(45) Date of Patent: Mar. 6, 2012

(54) AZALEA PLANT NAMED 'MNIHAR010'

(50) Latin Name: ***Rhododendron* sp.**
Varietal Denomination: MNIHAR010

(75) Inventor: James O. Harris, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 72 days.

(21) Appl. No.: 12/658,813

(22) Filed: Feb. 16, 2010

(65) Prior Publication Data

US 2011/0203022 P1 Aug. 18, 2011

(51) Int. Cl.
*A01H 5/00* (2006.01)

(52) U.S. Cl. ..... Plt./239; Plt./240

(58) Field of Classification Search ..... Plt./240, Plt./239, 238
See application file for complete search history.

*Primary Examiner* — Kent L Bell
(74) *Attorney, Agent, or Firm* — Jondle & Associates, P.C.

(57) ABSTRACT

A new and distinct variety of Azalea plant with spring and fall blooming, attractive, showy, dark pink single and semi-double flowers, easily propagated by semi-hardwood cuttings in late spring through summer, fast growth rate under normal fertilization and moisture conditions; upright, dense, and compact nature, grows well in containers, thrives in shade or sun and is hardy in Zone 6, is disclosed.

2 Drawing Sheets

Genus and species: *Rhododendron* sp.
Variety Denomination: 'MNIHAR010'.

BACKGROUND OF THE NEW PLANT

The present invention is a new and distinct variety of evergreen Azalea of the genus *Rhododendron*. This new Azalea, hereinafter referred to as 'MNIHAR010', was discovered in 1985 in Lawrenceville, Ga. 'MNIHAR010' originated from a planned cross hybridization between the female azalea plant 'Cherie' (also known as 'V 12-4') (unpatented) and the male azalea plant 'Indian Summer' (unpatented) in a controlled environment in Lawrenceville, Ga. The present invention has a unique blooming period, growth habit, and cold hardiness.

Asexual propagation of the new plant by semi-hardwood cuttings was performed at a nursery in Dearing, Ga. The new plant retains its distinctive characteristics and reproduces true to type in successive asexual propagations by semi-hardwood cuttings.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, dark pink flowers;
3. Numerous single and semi-double flowers;
4. Easily propagated by semi-hardwood cuttings in late spring through summer;
5. Fast growth rate under normal fertilization and moisture conditions;
6. Upright, dense, and compact nature;
7. Grows well in containers;
8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of plants that are 4-years old, grown in three-gallon containers in October in 2009 in Dearing, Ga.

DETAILED BOTANICAL DESCRIPTION OF THE NEW PLANT

Figure 1:
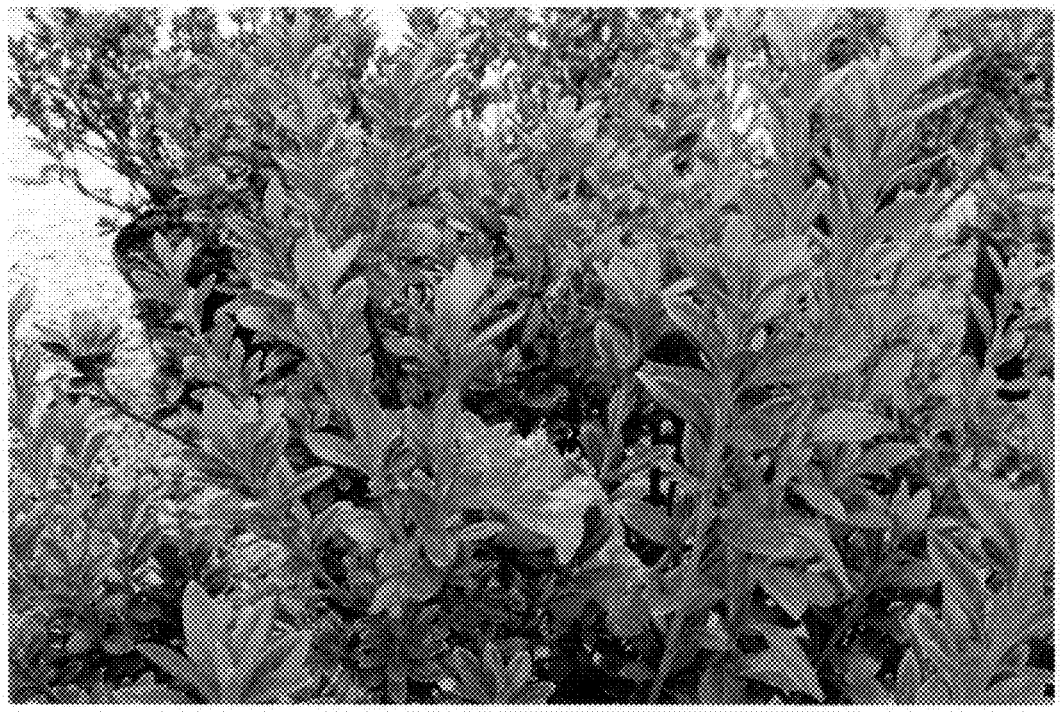
FIG. 1 is a close-up showing stems and mature foliage.
Figure 2:
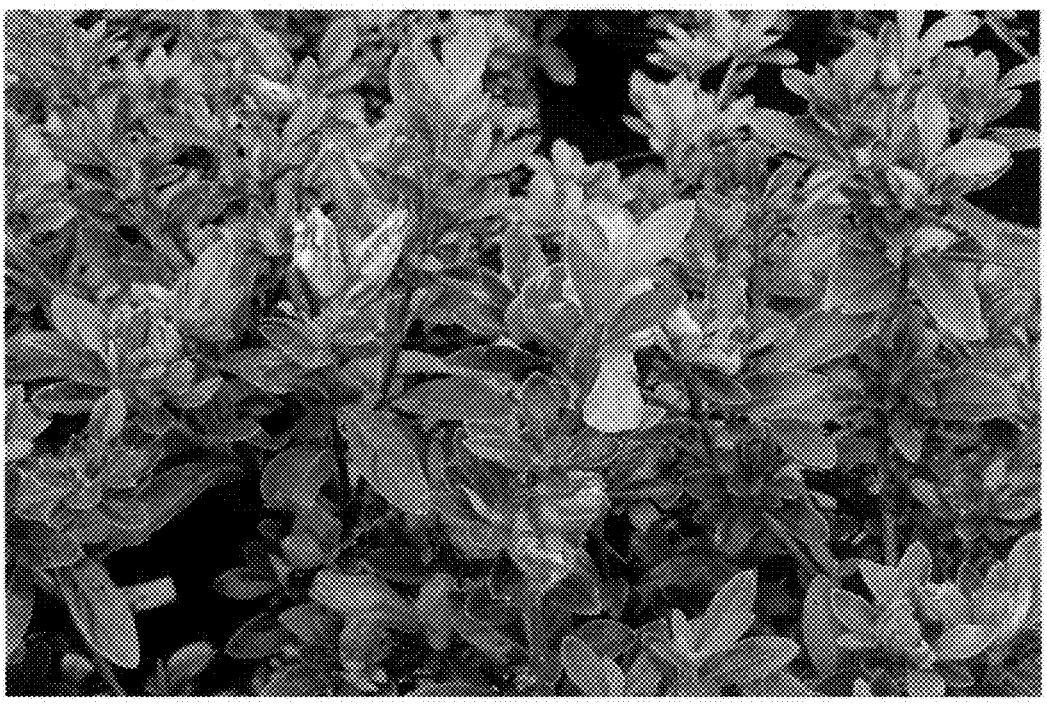
FIG. 2 is a close-up showing flower buds and immature foliage.
Figure 3:
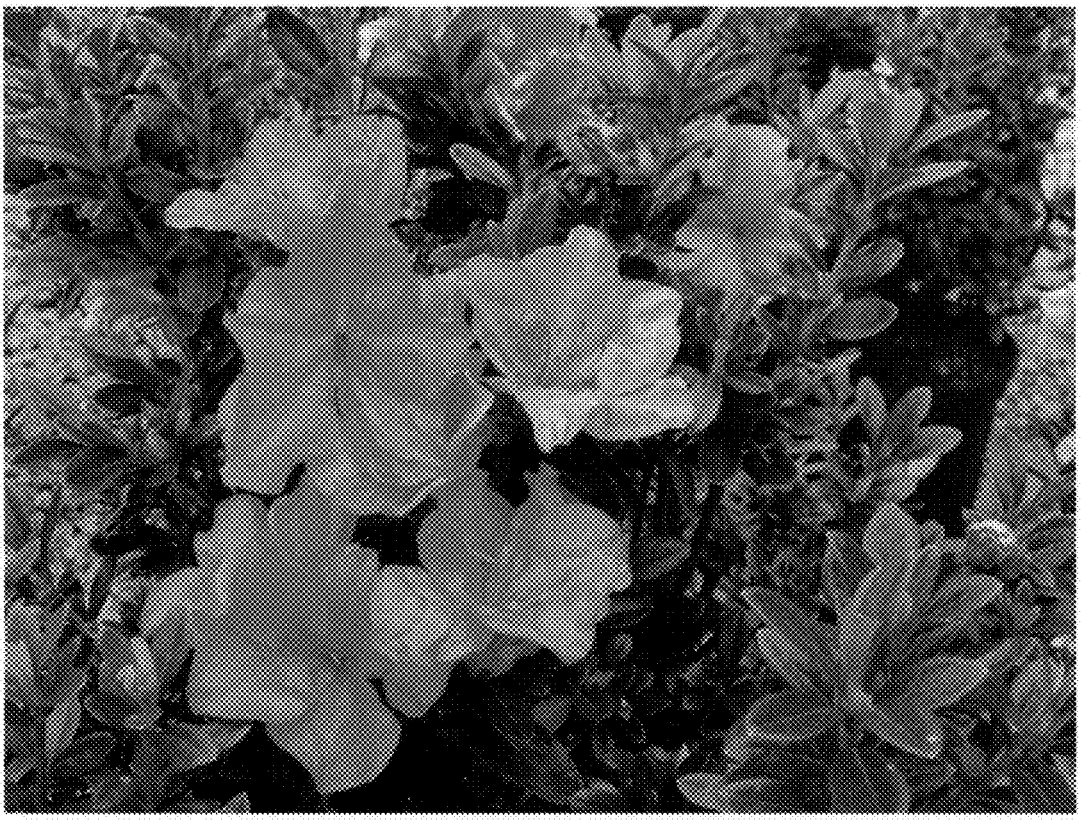
FIG. 3 is a close-up showing flower size, form, and color.

The following is a detailed description of the new variety of Azalea based on observations made of 4-year-old plants grown in a three-gallon containers according to wholesale commercial production conditions under full-sun and in an evaluation bed under semi-shade conditions in Dearing, Ga. in spring, summer, and fall in 2009. The colors of the various plant parts are detailed with reference to The Royal Horticultural Society Colour Chart (2001).

Classification:
- *Family.*—Ericaceae.
- *Species.*—*Rhododendron* sp.
- *Common name.*—Azalea.
- *Commercial name.*—'216I'.

Parentage:
- *Female parent.*—The azalea plant 'Cherie' (also known as 'V12-4') (unpatented).
- *Male parent.*—The azalea plant 'Indian Summer' (unpatented).

Growth:
- *Form.*—Compact, dense and rounded-upright.
- *Texture.*—Medium.
- *Height.*—137.16 cm to 152.4 cm.
- *Width.*—121.92 cm to 137.16 cm.
- *Growth habit.*—Upright and freely-branching.

*Growth rate.*—Medium growth rate under normal fertilization and moisture conditions. In a period of five years from a rooted cutting the plant reaches a height of 76.2 cm and a spread of 60.96 cm. The growth rate is normally about 10.16 cm to 15.24 cm per year; the plant reaches a height of 137.16 cm to 152.4 cm at maturity while maintaining a dense habit due to the abundant branch development.

*Spring growth.*—The date of initial spring growth is March 13, followed by continuous growth through fall.

*Life cycle.*—Perennial and evergreen.

Leaves:

*Arrangement.*—Alternate, simple, pubescent, and evergreen.

*Shape.*—Elliptic to broadly elliptic.

*Apex.*—Mucronate.

*Base.*—Attenuate.

*Margin.*—Entire.

*Length.*—3.4 cm.

*Width.*—1.4 cm.

*Venation pattern.*—Pinnate; the mid-veins and laterals are impressed on the upper surface and the prominent on the lower surface.

*Immature leaf.*—Upper surface: Color: Matte, RHS 145A (yellow-green) to RHS 143A (green). Pubescence: Strigose and scabrous; color is RHS N155A (white). Lower surface: Color: Matte, RHS 145A (yellow-green) to RHS 144A (yellow-green). Pubescence: Mainly strigose with some scabrous; color is RHS N155A (white) to RHS 159D (orange-white).

*Mature leaf.*—Upper surface: Color: Matte, RHS 139A (green). Pubescence: Strigose; color is RHS N155A; 0.1 cm in length.

*Lower surface.*—Color: Matte, RHS 138B (green). Pubescence: Strigose; color is RHS 165C (greyed-orange); 0.1 cm in length.

*Petiole.*—Length: 0.5 cm. Diameter: 0.1 cm. Pubescence: Pattern is strigose, length is 0.15 cm and color is RHS N155A (white) and RHS 159A (orange-white) and maturing to RHS 165A (greyed orange). Color: Begins as RHS 144B (yellow-green) and matures to RHS 146C (yellow-green).

Stems:

*Form.*—Densely branched.

*Young stems* (1-*year old and younger*).—Color: The distal end is RHS 178A (greyed-red) with RHS N155A strigose pubescence; the basal end is RHS N199C (grey-brown) with RHS N199C (grey-brown) pubescence.

*Second-year stems.*—Stem and pubescence color: RHS N199B (grey-brown) with RHS N199B (grey-brown) strigose pubescence. Length: 10 to 15 cm. Diameter: 0.5 cm. Pith: Solid and uniform. Internode length: Averages 0.6 cm in the full-sun and 0.7 cm in the shade at final point of stem elongation.

Flower buds:

*Arrangement and form.*—Tight; borne in groups of one or two sheathed by a pair of modified leaf bracts which are 1.6 cm in length, 0.4 cm in width, persistent and RHS 139A (green) at the apex and RHS 146B (yellow-green) at the base.

*Shape.*—Ovate.

*Apex.*—Acuminate.

*Base.*—Rounded.

*Length* (*at tight bud*).—0.9 cm.

*Diameter* (*at tight bud*).—0.5 cm.

*Color* (*of scales*).—Immature scales are RHS 145C (yellow-green) and mature to RHS N144C (yellow-green) with areas of RHS 185A (greyed-purple).

*Texture.*—Pubescent; villous pubescence emerges RHS N155A (white) and matures to RHS 165C (greyed-orange).

*Pedicel.*—Length: 1.0 cm. Diameter: 0.15 cm. Texture: Villous pubescence that is RHS N155A (white). Color: Apex end: RHS 44D (red). Basal end: RHS 145A (yellow-green).

*Calyx.*—Form and arrangement: Composed of 5 sepals in a cup-shape. Length: 0.5 cm. Width: 0.4 cm. Color: RHS 145A (yellow-green). Pubescence: Villous and some strigose that is RHS N155A (white) in color. Sepals: Shape: Incised broadly elliptical. Apex: Cuspidate to Obtuse. Base: Fused; joined at base to form a cup. Margin: Lobulate. Color (Both upper and lower surface): RHS 145A (yellow-green). Length: 0.5 cm. Width: 0.4 cm.

Flowers:

*Type.*—Perfect, single and semi-double flowers.

*Shape.*—Open funnel-shaped.

*Flowering habit and period.*—Borne on the current season's growth; 2 to 3 weeks beginning in mid-March to mid-April and late August until frost.

*Lastingness of flowers on the plant.*—4 to 7 days in the sun; 6 to 9 days in the shade.

*Fragrance.*—Absent.

*Diameter.*—5.6 cm.

*Depth.*—2.7 cm.

*Petals.*—Quantity per flower and arrangement: 5 imbricate petals that are fused at the base and remain fused up to 1.0 cm from the base and 2.0 cm from the base for the three petals with spots. Shape: Obovate. Apex: Rounded. Base: Fused. Margin: Entire and wavy. Texture (both upper and lower surfaces): Glabrous. Length (of petals without spots): 3.5 cm. Width (of petals without spots): 2.6 cm. Length (of petals with spots): 4.0 cm. Width (of petals with spots): 2.5 cm. Color: Both the upper and lower surfaces are RHS 52C (red); the upper surface of the three of the five petals have spots that are RHS 51A (red).

Reproductive parts:

*Pistil.*—Quantity and form: Single, non-petaloid. Length: 4.4 cm. Stigma: Color: RHS 187A (greyed-purple). Diameter: 0.1 cm. Style color: RHS 53B (red). Ovary: Pubescent, strigose, with 5 locules and is RHS N155A (white).

*Stamens.*—General: There are 5 stamens; the majority are petaloid (some range from 4 to 0 petaloid and 0 to 4 non-petaloid and vary in size and shape). Length: 3.1 cm. Filaments: Color: RHS 51C (red). Anthers: Color: RHS 183A (greyed-purple). Length: 0.15 cm. Width: 0.1 cm. Pollen amount: Moderate. Pollen color: RHS 155B (white).

Fruit:

*Maturity.*—The capsule matures in about 6 months in Dearing, Ga. and the fruit set is low and contains about 100-300 non-winged seeds.

*Length.*—0.7 cm.

*Width.*—0.3 cm.

*Color.*—RHS 146B (yellow-green).

CULTURE

'MNIHAR010' grows well in a wide range of conditions and tolerates sun to shade. '216I' prefers moist, well-drained soil that is rich in organic matter and responds well to mulching and medium applications of fertilizer. 'MNIHAR010' does best in soil with a pH of 5.0 to 5.5 and is propagated with semi-hardwood cuttings in late spring through the summer. Azaleas root in five to six weeks with high 80% plus percentage of rooting, tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIETIES

In Table 1, the 'MNIHAR010' is compared to parental varieties 'Cherie' (unpatented) and 'Indian Summer' (unpatented) and lists the differences between the varieties.

TABLE 1

| Characteristic | 'MNIHAR010' | 'Cherie' | 'Indian Summer' |
|---|---|---|---|
| Plant Height (Mature) | 137.16 cm to 152.4 cm | 91.44 cm to 152.4 cm | 243.84 cm to 304.8 cm |
| Flower Diameter | 5.6 cm | 5.08 cm | |
| Flower Form | Single and semi-double | Double | Single hose-in-hose to semi-double |
| Flower Color | Dark pink | Deep reddish orange | Yellowish pink |
| Bloom Period | Mid-March to Mid-April and late August until frost | Mid-April | Spring and Fall |
| Hardy Zone | 6 | 6 | 5 |
| Stamen Number | 5 | | 5 |
| Stamen Type | Petaloid and non-petaloid | Petaloid | Petaloid and non-petaloid |

When 'MNIHAR010' is compared to the commercial variety 'YBAZ-2028 Cotton Candy' (U.S. Plant Pat. No. 18,949), 'MNIHAR010' has smaller flowers (5.6 cm in diameter and 2.7 cm in depth) than 'YBAZ-2028 Cotton Candy' (7.5 cm in length and 3.25 cm in depth). Additionally, 'MNIHAR010' has dark pink flowers with darker pink spots, while 'YBAZ-2028 Cotton Candy' has red-purple flowers.

I claim:

1. A new variety of Azalea plant named 'MNIHAR010' as herein shown and described.

* * * * *